United States Patent
Gallazzo et al.

(10) Patent No.: US 6,287,800 B1
(45) Date of Patent: Sep. 11, 2001

(54) **PRODUCTION OF HIGH TITERS OF GIBBERELLINS, $GA_4$ AND $GA_7$, BY *GIBBERELLA FUJIKUROI* STRAIN LTB-1027**

(76) Inventors: Jorge L. Gallazzo, 1145 W. Knickerbocker Dr., Sunnyvale, CA (US) 94087; May D. Lee, 1335 Carbo Ct., Los Altos, CA (US) 94024

( * ) Notice: Subject to any disclaimer, the term of this patent is extended or adjusted under 35 U.S.C. 154(b) by 0 days.

(21) Appl. No.: 09/645,073

(22) Filed: Aug. 23, 2000

Related U.S. Application Data

(60) Provisional application No. 60/151,770, filed on Aug. 31, 1999.
(51) Int. Cl.[7] .............................. C12P 27/00; C12N 1/02
(52) U.S. Cl. ........................ 435/65; 435/254.1; 435/261; 435/262
(58) Field of Search .................................. 435/65, 254.1, 435/261, 262

(56) References Cited

FOREIGN PATENT DOCUMENTS

| | | |
|---|---|---|
| 0024951 | 12/1983 | (EP) . |
| 0112629 | 4/1987 | (EP) . |

OTHER PUBLICATIONS

Rademacher (1994) Plant Growth Regulation, vol. 15, pp. 303–314.*
Giordano et al. (1999) FEMS Microbiol. Letts., vol. 173, pp. 389–393.*
Agosin et al (1997) in Advances in Solid State Fermentation in Chapter 29 pp. 355–366.*
Kumar PKR and Lonsane BK. "Microbial Production of Gibberellins: State of the Art." Advances in Applied Microbiology. vol. 34: 29–139, 1989.
Bu'lock JD. "Ch. 13. Useful metabolites of Fusarium." In The applied mycology of Fusarium, Symposium of the British Mycological Society held at Queen Mary College, London, Sep. 1982, Ed by MO Moss & JE Smith. Cambridge University Press, Cambridge. pp. 215–229.
Bruckner B & Blechschmidt D. "The gibberellin fermentation." Critical Reviews in Biotechnology. 11(2): 163–192, 1991.
Mori, Shiozaki M, Itaya N, Matsui M and Sumiki Y. "Synthesis of substances related to gibberellins—XXI: Total synthesis of +/–gibberellins A2, A4, A9 and A10." Tetrahedron 25: 1293–1321, 1969.

Martin GC. "Ch. 11. Commercial uses of gibberellins." In The Biochemistry and Physiology of Gibberellins. vol. 2. Ed by A Crozier. Published by Praeger Scientific, New York City, pp. 395–444, (1983).
Shechter I & West CA. "Biosynthesis of Gibberellins: IV. Biosynthesis of cyclic diterpenes from trans–geranylgeranyl pyrophosphate." J Biol Chem 24(12): 3200–3209, 1969.
Fernandez–Martin R et al. "Gibberellin biosynthesis in gib mutants of *gibberella fujikuroi*." J Biol Chem 270(25):14970–14974, 1995.
Rachev R et al. "Gibberellin biosynthesis by fusarium moniliforme in the presence of hydrophobic resin Amberlite XAD–2." Bulg J Plant Physiol 23(1–2): 24–32, 1997. Abstract only.
Lange T, Kegler C, Graebe JE, Hedden P and Phillips AL. "Molecular characterisation of gibberellin 20–oxidases. Structure–function studies on recombinant enzymes and chimaeric proteins." Physiologia Plantarum 100(3): 543–549, (1997) Abstract only.
Kusaba S et al. "Alteration of hormone levels in transgenic tobacco plants overexpressing the rice homeobox gene OSH1." Plant Physiol pp 471–676 Feb. 1998. Abstract only.
Ross JJ, Murfet IC & Reid JB. "Gibberellin mutants." Physiologia Plantarum 100(3): 550–560. Abstract only (1997).

* cited by examiner

*Primary Examiner*—Jon P. Weber
*Assistant Examiner*—Harry J. Guttman

(57) ABSTRACT

A new method of producing a mixture of gibberellins which is predominantly $GA_4$ and $GA_7$ but also contains $GA_3$ has the steps of providing a seed of *Gibberella fujikuroi* Strain LTB-1027 or mutants derived therefrom, inoculating the seed into a culture medium rich in carbohydrate and relatively low in nitrogen, incubating the culture for at least four days, separating the *Gibberella fujikuroi* Strain LTB-1027 from the culture broth, and extracting the gibberellins to produce a gibberellin mixture which is at least 50% $GA_4$ and $GA_7$. The method produces a gibberellin mixture in which the combined titer of $GA_4$ and $GA_7$ exceeds 800 mg/liter. The production method also produces a gibberellin mixture with approximately equal titers of gibberellins $GA_4$ and $GA_7$. A variation of the method produces a gibberellin mixture which contains over 40% $GA_4$.

5 Claims, No Drawings

PRODUCTION OF HIGH TITERS OF GIBBERELLINS, GA₄ AND GA₇, BY *GIBBERELLA FUJIKUROI* STRAIN LTB-1027

CROSS-REFERENCE TO RELATED APPLICATIONS

This application claims the benefits of U.S. Provisional Application No. 60/151770, filed Aug. 31, 1999, and incorporated herein by reference.

FIELD OF INVENTION

This invention relates to a new strain of *Gibberella fujikuroi*, LTB-1027 for the production of gibberellins, $GA_3$, $GA_4$ and $GA_7$. It further relates to a method of producing gibberellins $GA_4$ and $GA_7$ at high titer by the fermentation of strain LTB-1027 under controlled conditions.

BACKGROUND OF THE INVENTION

Gibberellins are a large family of closely related tetracyclic triterpenoid compounds first discovered as metabolites of an Ascomycete, *Gibberella fujikuroi* (perfect state of *Fusarium moniliforme*), which causes the bakanae disease of rice seedlings. The disease is typified by excessive stem and leaf elongation. Infected seedlings became abnormally tall and spindly and usually fall over. The culture filtrate of *Gibberella fujikuroi* produced a similar growth-promoting effect. From the filtrate a crystalline active product, later shown to be a mixture of gibberellins, was isolated. Gibberellins assumed a wider significance when it was discovered that gibberellins (many of which have not been detected in *G. fujikuroi*) are endogenous plant growth hormones.

One hundred and twenty-one gibberellins have been described (http://www.plant-hormones.bbsrc.ac.uk/gibberellin_information2.htm) and named gibberellin $A_1$, $A_2$, $A_3$, $A_4$, $A_5$, . . . , approximately in the order they were discovered. Gibberellin $A_3$ ($GA_3$), $GA_4$, and $GA_7$ pertinent to this invention and their chemical structures are shown below.

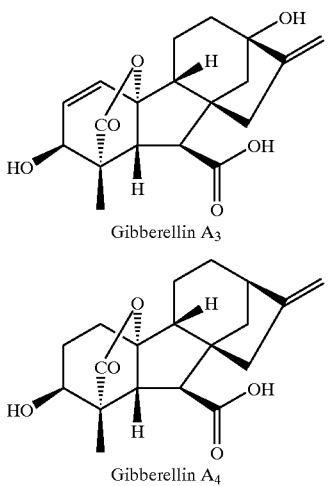

Gibberellin A₃

Gibberellin A₄

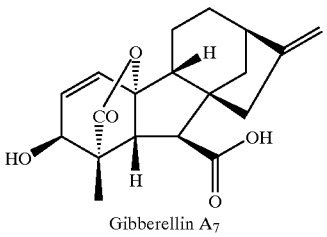

Gibberellin A₇

Since gibberellins are endogenous plant hormones, their concentrations in plant tissues are quite low and are tightly regulated. Immature seeds, the best source of plant derived gibberellins, contain 10–100 μg per gram wet weight. *Gibberella fujikuroi* is by far the most abundant source of the gibberellins, and $GA_3$ is usually the major gibberellin component. Fermentation titers of $GA_3$ at 1,000 mg/liter have been achieved in commercial production, although the actual titer is purported to be a few times higher, and titers of 2,000 mg/liter have been claimed (Bruckner, B. & Blechschmidt, D.: The Gibberellin Fermentation, Critical Reviews in Biotechnology, 11(2), 163–192 (1991)).

Different gibberellins stimulate the growth of different parts of plants and are effective during different periods of a plant's growth cycle. Gibberellin $A_3$ primarily stimulates the growth of stems and leaves, while $GA_4$ and $GA_7$ primarily stimulate flowering and cause fruit cells to elongate. Mixtures of $GA_4$ and $GA_7$ ($GA_{4+7}$) have been used successfully by growers of apples, pears and grapes to produce larger fruits and to achieve earlier harvests. The commercial production of $GA_4$ and $GA_7$, however, has not been quite as successful as that of $GA_3$, since $GA_4$ and $GA_7$ generally are minor metabolites of *Gibberella fujikuroi*. Titers of $GA_{4+7}$ at ~650 mg/liter with a $GA_4$/$GA_7$ ratio of 1:5~6 have been reported previously (ICI Patent, EP 0112629B, 29.04.87). Furthermore, the separation of $GA_4$ and $GA_7$ from a mixture containing both is difficult and has not been economically feasible; thus, $GA_4$ and $GA_7$ are available commercially only as mixtures with $GA_7$ as the predominant component. As fine chemicals, the costs of $GA_4$ and $GA_7$ are approximately 300 times that of $GA_3$.

Many other applications of $GA_{4+7}$ have been demonstrated and documented (Commercial uses of gibberellins, in *The Biochemistry and Physiology of Gibberellins*, Vol. 2, Crozier A., Ed., Praeger, New York, 1983). For example, the use of $GA_{4+7}$ for russet control of apples have demonstrated that the $GA_3$ in the $GA_{4+7}$ mixture caused reduction in flower bud formation and that $GA_4$ is most effective in russet control. $GA_4$ was found to be superior to $GA_3$ and $GA_{4+7}$ for promoting fruit set of many commercially grown apples. $GA_{4+7}$ was found to induce flowering in seed plants including many coniferous species (Pharis, R. P. & King, R. W.; Gibberellins & reproductive development in seed plants, Rev. Plant Physiol., 36, 517, 1985), as well as promote seed cone production (Ho, R. H., Gibberellin $A_{4+7}$ enhances seed cone production in field-grown black spruce, Can. J. For. Res., 18, 139, 1988), opening up the possibility of using $GA_{4+7}$ in forestry management.

A number of laboratories have searched for high producing strains of $GA_4$ and $GA_7$ that produce little or no $GA_3$. *Sphaceloma manihoticola*, a fungus that causes the super-elongation disease of cassava, produced $GA_4$ as the major gibberellin component (Graebbe, J. E., and Rademacher, W. B.; EP 0024951 B1). It also produced a number of other gibberellins, but no $GA_3$ and $GA_7$. The fermentation titer of $GA_4$, however, was only ~7 mg/liter and not of commercial importance. The laboratory of E. Cerda-Omedo reported a number of strains of *Gibberella fujikuroi* that produced $GA_7$ at the expense of $GA_3$ (Gibberellin Biosynthesis in gib mutants of *Gibberella fujikuroi*, J. Biol. Chem., 270:25, 14970–14974, 1995). The $GA_7$ titer, however, is only in the range of 60–80 mg/liter.

SUMMARY OF THE INVENTION

It is an object of this invention to employ a new mutant of *Gibberella fujikuroi* Strain LTB-1027 to produce mixtures of gibberellins that are high in the gibberellins $GA_4$ and $GA_7$. Another object of this invention is to produce gibberellins $GA_4$ and $GA_7$ in much higher titers than have been produced in the past.

The method disclosed herein produces a mixture of gibberellins which is predominantly $GA_4$ and $GA_7$ but also contains $GA_3$. The method has the following steps: a) providing a seed of *Gibberella fujikuroi* Strain LTB-1027 or mutants derived therefrom; b) inoculating the seed into a culture medium rich in carbohydrate and relatively low in nitrogen; c) incubating the culture for at least four days; d) separating the *Gibberella fujikuroi* Strain LTB-1027 from the culture broth; and e) extracting the gibberellins to produce a gibberellin mixture which is at least 50% $GA_4$ and $GA_7$.

In a preferred embodiment, the gibberellin mixture is at least 70% $GA_4$ and $GA_7$. In an even more preferred embodiment, the gibberellin mixture is at least 80% $GA_4$ and $GA_7$.

In another embodiment, the method yields a gibberellin mixture with a combined titer of $GA_4$ and $GA_7$ in excess of 800 mg/liter.

In yet another embodiment, the method of claim I yields a gibberellin mixture with approximately equal titers of gibberellins $GA_4$ and $GA_7$.

In a further embodiment, a disclosed method produces a gibberellin mixture which contains over 40% $GA_4$.

DESCRIPTION OF THE INVENTION

This invention describes the production of gibberellins by a mutant strain of *Gibberella fujikuroi*. This strain is capable of producing more than 1,000 mg/liter of a mixture of gibberellins in which the ratio of $GA_{4+7}$: $GA_3$ greater than 4:1 and there are approximately equal amounts of $GA_4$ and $GA_7$. It is expected that under the appropriate fermentation conditions, this strain can produce higher titers of $GA_4$ at the expense of $GA_7$. This strain was developed through repeated mutagenesis and strain selection starting from a *Gibberella fujikuroi* mutant that produced little $GA_3$. This strain is maintained in the MicroFerm Culture Collection of Microcide Pharmaceuticals, Inc., 850 Maude Avenue, Mountain View, CA 94043 as culture number LTB-1027. A viable culture of this new *Gibberella fujikuroi* strain has been deposited on Oct. 19, 1999, under conditions of the Budapest Treaty with the Patent Culture Collection Laboratory, National Center for Agricultural Utilization Research, Agricultural Research Service, U.S. Department of Agriculture, 1815 North University Street, Peoria, Illinois 61604 U.S.A. and has been added to its permanent collection. It has been assigned the strain designation NRRL 30227 by said depository.

Colonies of *Gibberella fujikuroi* LTB-1027 on Potato-Dextrose Agar (PDA) plates form aerial hyphae of the texture of cotton candy, 0.2–0.7 cm in height, white or light purple in color and orange-purple-brown substrate pigmentation.

Cultivation conditions of *Gibberella fujikuroi* suitable for the production of the gibberellins have been documented in two comprehensive reviews (Kumar, P. K. R. & Lonsane, B. K.; Microbial Production of Gibberellins: State of the Art, Advances in Applied Microbiology, Vol 34, 1989, pp.29–139; and Bruckner, B. & Blechschmidt, D.; The Gibberellin Fermentation, Critical Reviews in Biotechnology, 11(2), pp. 163–192, 1991). The fermentation of LTB-1027 for the production of the gibberellins may be carried out in a wide variety of liquid and solid culture media under aerobic fermentation conditions. Media similar to those used for the production of secondary metabolites, such as antibiotics, by microorganisms are suitable. In general, media that are useful contain sources of carbon and nitrogen assimilable by fungi and low levels of inorganic salts. In addition, the fermentation media may contain trace amounts of other elements, such as metals, necessary for the growth of the fungi and production of the desired secondary metabolites. These trace elements are usually present in sufficient concentration in the complex nutrient sources of carbon and nitrogen that may be used as nutrient sources, but can also be added separately to the medium if desired.

Carbohydrates such as sugars, for example glucose, dextrose, sucrose, maltose, lactose, and dextrin, corn meal, oat flour, starch, plant oils, molasses, skimmed milk, and milk whey are suitable sources of assimilable carbon in the culture media. The exact quantity of the carbon sources that is utilized in the medium will depend, in part, upon the other ingredients in the medium, but it is usually found that an amount of carbohydrate between 5 and 20% by weight of the medium is satisfactory. These carbon sources can be used individually or several such carbon sources may be combined in the same medium.

Various nitrogen sources such as ammonium sulfate, ammonium chloride, lysine, ammonium tartrate, yeast hydrolysate, yeast autolysates, yeast extracts, yeast cells, casein hydrolysate, tomato paste, corn meal, oat flour, soybean meal, peanut meal, cottonseed meal, and corn steep liquors are suitable sources of nitrogen in the culture media. The various sources of nitrogen can be used alone of in combination in amounts ranging from 1 to 5% by weight of the medium.

Among the nutrient inorganic salts, which can be incorporated in the culture media are the customary salts capable of yielding sodium, potassium, calcium, magnesium, ammonium, zinc, manganese, cobalt, phosphate, sulfate, chloride, carbonate, and borate. Trace elements such as molybdenum, copper, etc. are supplied as impurities of other constituents of the media.

It should be noted that the media described herein and in the Examples are merely illustrative.

The fermentation of *Gibberella fujikuroi*, LTB-1027, for the production of gibberellins can be conducted at temperatures ranging from 20° C. to 40° C., preferably 25–34° C. For optimum results it is most convenient to conduct these fermentations at a temperature in the range of 28–32° C. The pH of the culture medium suitable for producing the gibberellins can vary from 3.0 to 7.0 with a preferred range from 5.0 to 7.0. The length of time required for the fermentation is at least four days and may range from 4 to 15 days depending on the medium and exact fermentation conditions.

Small-scale fermentations are conveniently carried out by placing suitable quantities of nutrient medium in a flask by known sterile techniques, inoculating the flask with either spores or vegetative cellular growth of *Gibberella fujikuroi*

LTB-1 027 and loosely closing the flask with cotton wool or foam plugs. Fermentation is allowed to proceed in a temperature and humidity controlled environment. Fermentations in liquid media are maintained on a reciprocating or rotary shaking device to achieve optimal aeration; fermentations in solid media are allowed to remain stationary.

For larger-scale work, it is preferable to conduct the fermentation in liquid medium and in suitable tanks provided with an agitator and a means of aerating the fermentation medium. The nutrient medium is made up in the tank, sterilized and inoculated with a vegetative cellular growth of *Gibberella fujikuroi* LTB-1027. The fermentation is allowed to continue at a prescribed temperature for a prescribed number of days while agitating and/or aerating the fermentation mixture. During the fermentation period, higher titers of gibberellins can be achieved by supplementing the fermentation with suitable amounts of carbon source, such as glucose and soluble starch, to prolong the production phase of the fermentation. Supplementation can be performed by continuous feeding or batch feeding.

Fermentations were monitored for the production of $GA_3$, $GA_4$, and $GA_7$ by analytical HPLC using the following conditions:

Column: Kromasil C18 (0.46×10 cm, 5 micron particle, Hichrom KR100-5C18-100A)

Solvent: Methanol: 1% acetic; 30/70 (v/v) for 2 minutes, linear gradient to 70/30 (v/v) over 10 minutes, hold at 70/30 (v/v) for 5 Minutes Flow Rate: 1 ml/min Detection: Evaporative Light Scattering (Sedex 55 ELS Detector)

Retention: 6.0 min for $GA_3$, 13.4 min for $GA_7$, and 13.9 min for $GA_4$

Calibration curves used for quantitating $GA_3$, $GA_4$ and $GA_7$ in fermentation samples were established using solutions containing known concentrations of each of the three gibberellins prepared from authentic samples purchased from Sigma Chemical Company.

A number of methods of isolation of gibberellin mixtures and of selected gibberellins have been developed. The first technique was adsorption on active carbon. Later, gibberellins were isolated by liquid-liquid extraction of the culture filtrate with water-immiscible organic solvents. Solvents for this procedure include ethyl acetate or butyl acetate. Useful organic solvents include ethyl methyl ketone, methyl isobutyl ketone, n-butanol and diethyl ether. Initially the pH of the culture filtrate is adjusted to pH2 with hydrochloric acid and extracted with ethyl acetate or methyl isobutyl ketone. From this extract, gibberellins may be recovered by adsorption on solid sodium or potassium bicarbonate or by buffer-solvent processes, taking advantage of the relative solubilities of the free acid in solvent and of the alkaline salt in an aqueous phase. The buffer solvent process may use water containing a slight excess of sodium bicarbonate giving a pH of about 7.

Gibberellins also have been recovered on ion-exchange resins that bind $GA_3$. First, other impurities (organic acids, proteins and pigments) are precipitated from the culture filtrate by addition of an alkaline earth metal hydroxide such as $Ba(OH)_2$. Gibberellins remain in a filtrate that is then passed through a weak cation-exchange resin (Amberline IEC 50, H-form) and a weak anion-exchange resin (Ambolite IR 4B, acetate or formate form). Gibberellins are eluted by slow percolation with ammonia or alkaline buffers of ammonia salts.

The gibberellin product of the ion-exchange columns can be further purified by extraction by ethyl acetate and crystallization. Subsequent purification steps include dissolving the crystals in water to which active carbon is added to bind impurities, extracting the purified solution with ethyl acetate, evaporating, washing and drying. Purification also can be performed by ion-exchange chromatography.

Three methods for separating $GA_3$ from a $GA_4/GA_7$ mixture have been disclosed. In one, the culture filtrate is mixed with a water-immiscible solvent, such as ethyl acetate, at a pH between 4 and 8.5. The organic extract is enriched for $GA_4/GA_7$. The aqueous solution is rich in $GA_3$. In the second method, after organic extraction, N-hydroxycarbyl-N-arylmethyl amines are added to produce amine salts of $GA_4$ and $GA_7$. These amine salts precipitate selectively leaving $GA_3$ in solution. The $GA_4$ and $GA_7$ salts are isolated by filtration. A third method starts with the $GA_4$ and $GA_7$ amine salts, which are reacted with organic acid and filtered. There is no known procedure for separating $GA_4$ and $GA_7$.

The gibberellins produced by the methods disclosed herein can be further isolated and purified by methods known in the art, including ICI Patent, EP 0112629B, 29.04.87. This will result in highly purified mixtures of $GA_4$ and $GA_7$, with even less $GA_3$ present.

Further mutations of *Gibberella fujikuroi* Strain LTB-1027 can be made by conventional methods, such as UV radiation, fast neutrons and X-ray treatment of nonsporulating organisms. Mutation methods also may be combined, such as UV and ethylenimine.

The following illustrative and non-limiting examples are provided in order that the invention may be more fully understood.

EXAMPLE 1

Preservation of *Gibberella fujikuroi* LTB-1027

LTB-1027 was maintained as a spore suspension at −80° C. and was recovered by plating a small aliquot of the spore suspension on potato-dextrose agar (PDA).

| Composition of Potato-Dextrose Agar (PDA) | |
|---|---|
| Agar | 15 g/l |
| Potatoes, infusion from | 200 g/l |
| Dextrose | 20 g/l |

Final pH 5.6

Mycelia and spores from strain LTB-1027 grown on a PDA plate were harvested with a 16% sterile solution of glycerol. Aliquots (1ml) of the spore suspension were dispensed in sterile cryovials and maintained at −80° C. This master stock maintained at −80 C. is the starting point of all subsequent fermentations. PDA slants of LTB-1027 were prepared by inoculating 0.1 ml of the master stock on sterile PDA slants and incubating the inoculated slants for 5–7 days at 30° C. Mature PDA slants of LTB-1027 have low-lying, mauve aerial mycelium, and orange-brown substrate pigmentation and can be stored at 40° C. for up to 6 weeks as working slants. When fermentation of LTB-1027 was required, spores and mycelial growth on working slants were harvested with sterile 16% solution of glycerol and used to inoculate the seed medium.

EXAMPLE 2

Production of $GA_3$, $GA_4$ and $GA_7$ by LTB-1027 in Shake Flasks

A. Seed Preparation

| Composition of Seed Medium | |
|---|---|
| Glucose | 10 g/l |
| Soluble starch | 10 g/l |
| Soybean flour | 15 g/l |
| $(NH_4)_2SO_4$ | 0.5 g/l |
| $KH_2PO_4$ | 1.2 g/l |
| $MgSO_4$ | 0.8 g/l |

No pH adjustment

Except for soluble starch (Difco) and $MgSO_4$ (EM Scientific), the ingredients were supplied by Sigma. The seed medium was prepared according to the formula above with deionized water, and 50 ml was dispensed into each 250-ml Erlenmeyer flasks. The flasks were closed with foam plugs and were sterilized at 121° C. for 20 minutes. One LTB-1027 agar slant prepared as described in Example 1 was harvested with 5 ml sterile 16% solution of glycerol to form a suspension. This suspension was inoculated into two 250-ml flasks containing 50-ml of the seed medium. The inoculated flasks were incubated in an environmental chamber equipped with 2-inch-throw reciprocating shaking platforms. The seed was grown at 28° C. with 85% relative humidity and shaken at 220 rpm for 48 hours.

B. Fermentation

| Composition of Fermentation Medium | |
|---|---|
| Soluble starch | 65 g/l |
| Glucose | 10 g/l |
| Soybean flour | 15 g/l |
| $KH_2PO_4$ | 1.5 g/l |
| $MgSO_4$ | 0.8 g/l |
| $ZnCl_2$ | 0.01 g/l |
| $(NH_4)_2SO_4$ | 0.4 g/l |
| Boric acid | 0.01 g/l |
| $CaCO_3$ | 3.0 g/l |

PH adjusted to 5.6 before $CaCO_3$ addition

As for ingredient sources, the same suppliers were used as disclosed above; the other ingredients also were obtained from Sigma. The fermentation medium was prepared according to the formula above with deionized water, and 50 ml was dispersed into each 250-ml Erlenmeyer flask. The flasks were closed with foam plugs and were sterilized at 121° C. for 20 minutes. Each flask containing 50 ml of the sterilized medium was inoculated with 5 ml of LTB-1027 seed prepared as described in Section A. The inoculated flasks were incubated in an environmental chamber equipped with 2-inch-throw, reciprocating shaking platforms. The fermentation proceeded at 28° C. with 85% relative humidity and shaking at 220 rpm.

At the designated fermentation elapsed time, three flasks were removed from the environmental chamber, and the content of each was centrifuged to separate mycelium and fermentation beer. The amounts of $GA_3$, $GA_4$ and $GA_7$ present in each fermentation beer were determined by high-pressure liquid chromatography using the system described above in The Description of the Invention. The average fermentation titers of $GA_3$, $GA_4$, and $GA_7$ of the three flasks harvested at each fermentation elapsed time are shown in the table below. The resulting mixtures have an excess of $GA_4$ and $GA_7$. Moreover, $GA_4$ is approximately 40% of the mixture. This mixture should be particularly valuable in the apple industry, where $GA_4$ has been found more effective in russet control and in promoting fruit set.

| Fermentation Elapsed Time (days) | Gibberellin $A_3$ (mg/l) | Gibberellin $A_7$ (mg/l) | Gibberellin $A_4$ (mg/l) |
|---|---|---|---|
| 4 | 130 | 140 | 220 |
| 5 | 140 | 150 | 260 |
| 6 | 150 | 160 | 290 |
| 7 | 150 | 170 | 290 |

EXAMPLE 3

Production of $GA_3$, $G_4$ and $GA_7$ by LTB-1027 in 20-Liter Fermenter

A. Seed Preparation

Four LTB-1027 agar slants were prepared as described in Example 1. Each slant was harvested with 5 ml sterile 16% glycerol solution to give 20 ml of combined spore and cell suspension. Into each of eight 500-ml Erlenmeyer flasks containing 150 ml of seed medium prepared as described in Example 2.A, 2.5 ml of the glycerol suspension was inoculated. The inoculated flasks were incubated in an environmental chamber equipped with 2-inch-throw, reciprocating shaking platforms. The seed was grown at 28° C. with 85% relative humidity and shaken at 220 rpm for 48 hours.

B. Fermentation

Ten liters of fermentation medium prepared as described in Example 2. B were placed in a 20-liter fermenter (BioFlo IV, New Brunswick Scientific). Five ml of Antifoam 289 (Sigma) was added, and the medium was sterilized at 120° C. for 30 minutes. Upon cooling to room temperature, the medium in the fermenter was inoculated with 1.2 liter of seed prepared as in Section A. Fermentation was allowed to proceed at 28° C. with initial aeration at 5 liters of sterile air per minute (5 l/min) and initial agitation at 200 rpm. Dissolved oxygen concentration in the fermentation mixture dropped to 30% of air saturation and was maintained at this value by adjusting the agitation speed of the impellers and the airflow. Samples were withdrawn from the fermenter daily and assayed for the titer of gibberellins as described in Experiment 2. B. The titers of $GA_3$, $GA_4$ and $GA_7$ in the fermentation mixture at 2, 3, 4, 5, and 6 days after the start of the fermentation are shown below.

| Fermentation Elapsed Time (days) | Gibberellin $A_3$ (mg/l) | Gibberellin $A_4$ (mg/l) | Gibberellin $A_7$ (mg/l) |
|---|---|---|---|
| 2 | 100 | 140 | 150 |
| 3 | 130 | 260 | 280 |
| 4 | 140 | 290 | 300 |
| 5 | 180 | 420 | 430 |
| 6 | 140 | 320 | 330 |

EXAMPLE 4

Characterization of Strain LTB-1027

Strain LTB-1027 was further characterized by its genomic nucleotide sequence in the region that includes the 18S rRNA gene, ITS1, the 5.8S rRNA gene, and ITS2 (SEQ ID NO 1). ITS1is the internal transcribed spacer (ITS) region 1 located between the 18S and the 5.8S rRNA genes, and ITS2 is located between the 5.8S and the 26S rRNA genes. The DNA sequences of the ITS regions are much more variable than those of the rRNA genes and have been used for species and strain differentiation (Bruns, T. D., T. J. White, and J. W. Taylor, 1991, Annu. Rev. Ecol. Syst., 22:525–564; Summerbell, R., R. A. Haugland, A. Li. and A. K. Gupta, 1999, J. Clinical Microbiology, 37:12, 4005–4011; Henry, T., P. C. Iwen, and S. H. Hinrichs, 2000, J. Clinical Microbiology, 38:4, 1510–1515).

The DNA sequencing was performed using standard techniques on an Applied Biosystems DNA Sequencer Model #377 (Foster City, Calif.). The rRNA coding sequences of fungi are repeated in approximately 100 different places throughout the genome. Variable bases are residues numbered 1778, 1780, 1793, 1797, 1822, 1947, 2144, and 2321. In SEQ ID NO 1, the residues 1–1774 comprise the 18S rRNA gene, residues 1775–1921 comprise the ITS1 region, residues 1922–2078 comprise the 5.8S rRNA gene, residues 2079–2243 comprise the ITS2 region, and residues 2244–2293 comprise part of the 28S rRNA gene.

Having now fully described the invention by way of illustration and examples for purposes of clarity and understanding, it will be apparent to those of ordinary skill in the art that certain changes and modifications may be made in the disclosed embodiments and such modifications are intended to be within the scope of the present invention.

What is claimed is:

1. A method of producing a mixture of gibberellins which is at least 70% GA$_4$ and GA$_7$, said method comprising the steps of
   a) providing a seed of *Gibberella fujikuroi* strain LTB-1027, or a mutant derived having the identifying characteristics of said strain;
   b) inoculating the seed into a culture medium containing about 0.4 grams/liter of a nitrogen source and about 75 grams/liter of a carbohydrate source;
   c) incubating the culture for 4–7 days;
   d) separating the Gibberella from the culture broth; and
   e) collecting the culture broth,
   whereby the culture broth contains a mixture of gibberellins which is at least 70% GA$_4$ and GA$_7$.

2. The method of claim 1 wherein the gibberellin mixture is at least 80% GA$_4$ and GA$_7$.

3. The method of claim 1 wherein the gibberellin mixture has a combined titer of at least 800 mg/liter.

4. The method of claim 1 wherein the gibberellin mixture has approximately equal titers of gibberellins GA$_4$ and GA$_7$.

5. The method of claim 1 wherein the gibberellin mixture is about 35% to about 50% GA$_4$.

* * * * *

SEQUENCE LISTING

<160> NUMBER OF SEQ ID NOS: 1

<210> SEQ ID NO 1
<211> LENGTH: 2293
<212> TYPE: DNA
<213> ORGANISM: Gibberella fujikuroi

<400> SEQUENCE: 1

```
caatatgctt gtctcaaaga ttaagccatg catgtctaag tataagcaat tatacagcga      60
aactgcgaat ggctcattat ataagttatc gtttatttga tagtaccttA ctacttggat     120
aaccgtggta attctagagc taatacatgc taaaaatccc gacttcggaa gggatgtatt     180
tattagatta aaaaccaatg cccttcgggg ctcactggtg attcatgata actcctcgaa     240
tcgcatggcc ttgtgccggc gatggttcat tcaaatttct tccctatcaa ctttcgatgt     300
ttgggtattg gccaaacatg gttgcaacgg gtaacggagg gttagggctc gacccggag      360 aaggagcctg agaaacggct actacatcca aggaaggcag caggcgcgca aattacccaa     420
tcccgacacg gggaggtagt gacaataaat actgatacag ggctctttg ggtcttgtaa      480 ttggaatgag tacaatttaa atcccttaac gaggaacaat tggagggcaa gtctggtgcc    540
agcagccgcg gtaattccag ctccaatagc gtatattaaa gttgttgtgg ttaaaaagct    600
cgtagttgaa ccttgggcct ggctggccgg tccgcctcac cgcgtgtact ggtccggccg    660
ggcctttccc tctgtggaac cccatgccct tcactgggtg tggcggggaa acaggacttt    720
tactgtgaaa aaattagagt gctccaggca ggcctatgct cgaatacatt agcatggaat    780
aatagaatag gacgtgtggt tctattttgt tggtttctag gaccgccgta atgattaata    840
gggacagtcg ggggcatcag tattcaattg tcagaggtga aattcttgga tttattgaag    900
actaactact gcgaaagcat ttgccaagga tgttttcatt aatcaggaac gaaagttagg    960
ggatcgaaga cgatcagata ccgtcgtagt cttaaccata aactatgccg actagggatc   1020
ggacggtgtt attttttgac ccgttcggca ccttacgaga aatcaaagtg cttggctcc    1080 aggggagta tggtcgcaag gctgaaactt aaagaaattg acggaagggc accaccaggg    1140
gtggagcctg cggcttaatt tgactcaaca cggggaaact caccaggtcc agacacaatg    1200
aggattgaca gattgagagc tctttcttga ttttgtgggt ggtggtgcat ggccgttctt    1260
agttggtgga gtgatttgtc tgcttaattg cgataacgaa cgagaccttA acctgctaaa    1320
tagcccgtat tgctttggca gtacgctggc ttcttagagg gactatcggc tcaagccgat    1380
ggaagtttga ggcaataaca ggtctgtgat gcccttagat gttctgggcc gcacgcgcgc   1440
```

-continued

```
tacactgacg gagccagcga gtacttcctt gtccgaaagg tccgggtaat cttgttaaac    1500
tccgtcgtgc tggggataga gcattgcaat tattgctctt caacgaggaa tccctagtaa    1560
gcgcaagtca tcagcttgcg ttgattacgt ccctgcectt tgtacacacc gcccgtcgct    1620
actaccgatt gaatggctca gtgaggcgtc cggactggcc cagagaggtg ggcaactacc    1680
actcagggcc ggaaagctct ccaaactcgg tcatttagag gaagtaaaag tcgtaacaag    1740
gtctccgttg gtgaaccagc ggagggatca ttaccgagtt tacaactccc aaaccectgt    1800 gaacatacca attgttgcct cggcggatca gcccgctccc ggtaaaacgg gacggcccgc    1860
cagaggaccc ctaaactctg tttctatatg taacttctga gtaaaaccat aaataaatca    1920
aaactttcaa caacggatct cttggttctg gcatcgatga agaacgcagc aaaatgcgat    1980
aagtaatgtg aattgcagaa ttcagtgaat catcgaatct ttgaacgcac attgcgcccg    2040
ccagtattct ggcgggcatg cctgttcgag cgtcatttca accctcaagc ccccgggttt    2100
ggtgttgggg atcggcgagc ccttgcggca agccggcccc gaaatctagt ggcggtctcg    2160
ctgcagcttc cattgcgtag tagtaaaacc ctcgcaactg gtacgcggcg cggccaagcc    2220
gttaaacccc caacttctga atgttgacct cggatcaggt aggaataccc gctgaactta    2280
agcatatcaa taa                                                       2293
```